US010925634B2

(12) United States Patent
Tia et al.

(10) Patent No.: US 10,925,634 B2
(45) Date of Patent: Feb. 23, 2021

(54) NEEDLE GUIDE SYSTEM FOR USE IN A MEDICAL PROCEDURE

(71) Applicant: Harmonus, Inc., Lowell, MA (US)

(72) Inventors: Peter Tia, Dracut, MA (US); Phillip John Marathakis, Cambridge, MA (US)

(73) Assignee: HARMONUS, INC., Lowell, MA (US)

( * ) Notice: Subject to any disclaimer, the term of this patent is extended or adjusted under 35 U.S.C. 154(b) by 157 days.

(21) Appl. No.: 16/195,169

(22) Filed: Nov. 19, 2018

(65) Prior Publication Data

US 2019/0192186 A1 Jun. 27, 2019

Related U.S. Application Data

(60) Provisional application No. 62/589,870, filed on Nov. 22, 2017.

(51) Int. Cl.
*A61B 17/34* (2006.01)
*A61B 10/02* (2006.01)
(Continued)

(52) U.S. Cl.
CPC ...... *A61B 17/3403* (2013.01); *A61B 10/0241* (2013.01); *A61B 90/39* (2016.02);
(Continued)

(58) Field of Classification Search
CPC .. A61B 10/0241; A61B 90/39; A61B 17/3403
See application file for complete search history.

(56) References Cited

U.S. PATENT DOCUMENTS

| 4,798,212 A | 1/1989 | Arana |
| 5,871,448 A * | 2/1999 | Ellard .................. A61B 8/0841 |
| | | 600/459 |

(Continued)

OTHER PUBLICATIONS

James, Lee A., and Schwenk, Earl B. Fatigue-Crack Propagation Behavior of Type 304 Stainless Steel at Elevated Temperatures. Metallurgical Transactions, vol. 2, Issue 2, Feb. 1971 pp. 491-496.

*Primary Examiner* — Richard G Louis
(74) *Attorney, Agent, or Firm* — Burns & Levinson LLP; Bruce D. Jobse

(57) ABSTRACT

A sterile needle guide system for directing needle entry during a medical procedure includes a needle guide plate extending in a plane and having a plurality tubular needle guides extending through the plate at an normal angle to the plane of the plate. A movable base translatable along an axis normal to the plane of the plate defines features to removably receiving the plate. A calibrator attachment is removably securable to the needle guide plate and enables attachment of the needle guide plate to the base and calibration of the needle guide position in a sterile manner. In embodiments, the movable base includes a base body, a rail component over which the base body is movably coupled, and a ratchet mechanism for releasably securing the base body to the rail component. The disclosed needle guide system enables the needle guide plate to be positioned directly adjacent to the patient's perennial to reduce the curvature of deflection of the needle upon entry into the patient's body during the biopsy procedure.

15 Claims, 9 Drawing Sheets

(51) Int. Cl.
*A61B 90/00* (2016.01)
*A61B 17/00* (2006.01)
(52) U.S. Cl.
CPC ..... *A61B 90/37* (2016.02); *A61B 2017/00407* (2013.01); *A61B 2017/3411* (2013.01); *A61B 2090/3983* (2016.02)

(56) References Cited

U.S. PATENT DOCUMENTS

| | | |
|---|---|---|
| 6,540,656 B2 | 4/2003 | Fontayne et al. |
| 7,658,879 B2 | 2/2010 | Solar |
| 8,474,122 B2 | 7/2013 | Melsheimer |
| 9,414,815 B2 | 8/2016 | Miller |
| 9,681,919 B2 | 6/2017 | Glossop |
| 9,743,912 B2 | 8/2017 | Fichtinger et al. |
| 2009/0156961 A1 | 6/2009 | Tsonton et al. |
| 2009/0194446 A1 | 8/2009 | Miller et al. |
| 2009/0292244 A1* | 11/2009 | Flagle ............. A61B 17/3403 604/116 |
| 2010/0122926 A1 | 5/2010 | Tocco et al. |
| 2011/0082387 A1 | 4/2011 | Miller et al. |
| 2011/0105823 A1 | 5/2011 | Single, Jr. et al. |
| 2011/0152714 A1* | 6/2011 | Luginbuhl ......... A61B 17/3403 600/562 |
| 2014/0142420 A1 | 5/2014 | Jackson |
| 2016/0008074 A1 | 1/2016 | Glossop |

* cited by examiner

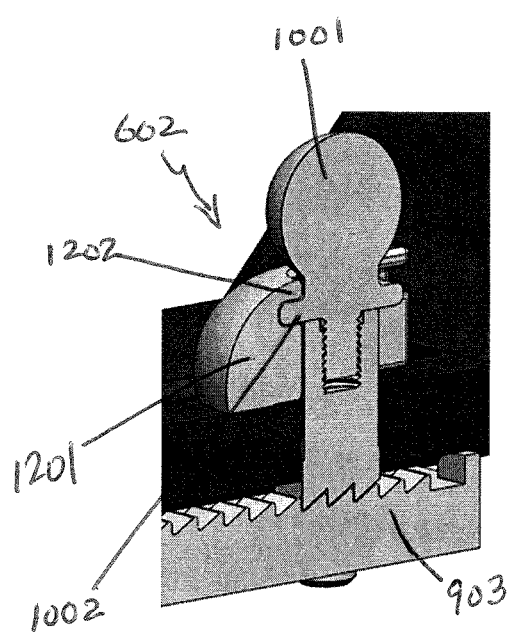
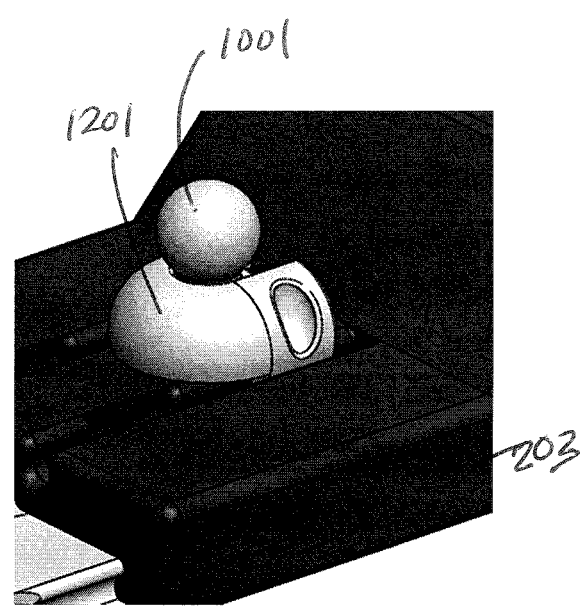
Figure 12 A                    Figure 12B

NEEDLE GUIDE SYSTEM FOR USE IN A MEDICAL PROCEDURE

BACKGROUND OF THE DISCLOSURE

Prostate cancer is a leading cause of cancer death in the United States. Over 225,000 cases of cancer were diagnosed in 2014 with almost 30,000 deaths. Prostate cancer is treatable, if properly diagnosed. The initial screen to identify men with prostate cancer is the level of prostate-specific antigen PSA in blood. These men are often referred for a core biopsy in which samples of the prostate are excised and evaluated by a pathologist to determine if cancerous cells are present. There is no information in a PSA blood test to determine where cancerous tissue might be found in the prostate. A 12-core sampling distributed over the prostate has become the accepted method to determine if cancer is present. The procedure is typically conducted using a trans-rectal ultrasound to visualize the needle location, and the needle is typically inserted through the lining of the rectum to reach the prostate. The trans-rectal ultrasound-guided procedure requires a large number of needle insertions, requires high doses of antibiotic prophylaxis, does not make the suspicious region easily visible, and provides no means of recording sample locations for future reference.

Accordingly, a need exists for reducing the number of needle insertions in a prostate biopsy procedure and the need for antibiotics by avoiding accessing the prostate through the rectum.

A further need exists for a technique which can provide a precise positioning of the needle tip during a biopsy.

An even further need exists for a means for directing needle entry during a medical procedure, such as an MRI-guided prostate biopsy, and which can be placed in the bore of the MRI scanner device.

SUMMARY OF THE DISCLOSURE

Disclosed is a needle guide system for directing needle entry during a medical procedure, such as an MRI-guided prostate biopsy. In embodiments, the system comprises a needle guide plate, calibrator and movable base. The needle guide plate includes a matrix of needle guide channels. The needle guide plate is insertable into the movable base which is capable of decreasing the distance between the needle guide plate and the skin surface to prevent deflection of the needles at the point of entry. Fiducial markers on the calibrator which is removably attached to the needle guide plate provide points of reference to calculate which of the needle guide channels should be used to guide a needle during a biopsy procedure. The disclosed needle guide system enables the needle guide plate to be positioned directly adjacent to the patient's perennial to reduce the curvature of deflection of the needle upon entry into the patient's body during the biopsy procedure.

Also disclosed is a method for directing needle entry during a medical procedure, such as an MRI-guided prostate biopsy while the patient remains in the MRI. The target locations can be identified in a reference frame of the scanner using initial images and pre-operative multi-parameter MRI, and trajectories selected accordingly.

According to one aspect of the disclosure, a sterile needle guide system for directing needle entry during a medical procedure comprises: a needle guide plate extending in a plane and having a plurality tubular needle guides extending through the plate at an angle to the plane of the plate; and a movable base translatable along an axis normal to the plane of the plate and defining features to removably receiving the plate. In embodiments, the system further comprises a calibrator attachment removably securable to the needle guide plate. In embodiments, the movable base comprises a base body, a rail component over which the base body is movably coupled, and a ratchet mechanism for releasably securing the base body to the rail component.

According to another aspect of the disclosure, a sterile needle guide kit for use during medical procedure comprises: a needle guide plate extending in a plane and having a plurality tubular needle guides extending through the plate at an normal angle to the plane of the plate; a movable base translatable along an axis relative to the plane of the plate and defining features to removably receiving the plate; a calibrator attachment removably securable to the needle guide plate. In embodiments, the movable base comprises a base body, a rail component over which the base body is movably coupled, and a ratchet mechanism for releasably securing the base body to the rail component.

According to yet another aspect of the disclosure, a method for directing needle entry during a medical procedure comprising: A) providing a base movably along an axis and removably securable to a needle guide plate having a plurality of fiducial markers in a plane normal to the axis and a plurality of needle guide channels extending through the needle guide plate parallel to the axis; B) securing the movable base along the axis; C) securing the sterile needle guide plate to the movable base; D) positioning the movable base along the axis; E) obtaining a frame of reference from the plurality of fiducial markers attached to the needle plate; F) determining a position of at least one needle guide channels relative to the fiducial markers; and G) inserting a needle into at least one needle guide channels.

DESCRIPTION THE DRAWINGS

Various aspects of the present disclosure are described hereinbelow with reference to the drawings, wherein.

Figure 8:
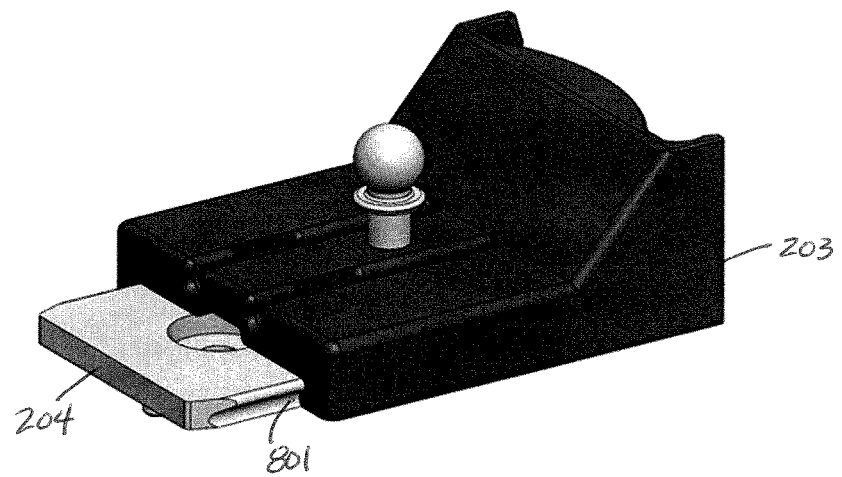
FIG. 8 illustrates conceptually the movable base (unlocked) sliding along a rail portion thereof in accordance with the present disclosure.
Figure 10A:
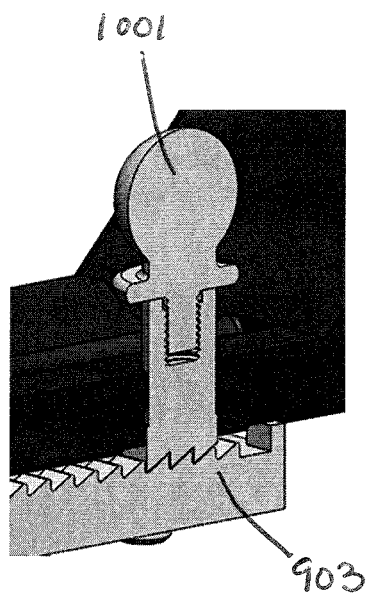
Figure 10B:
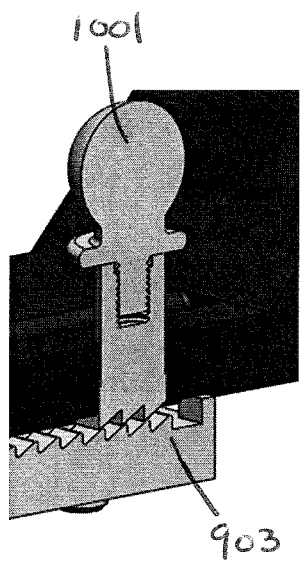
Figure 10C:
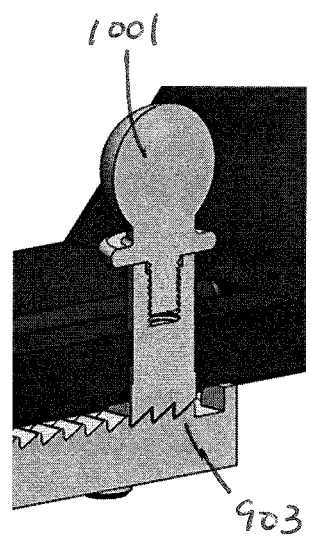
Figure 11:
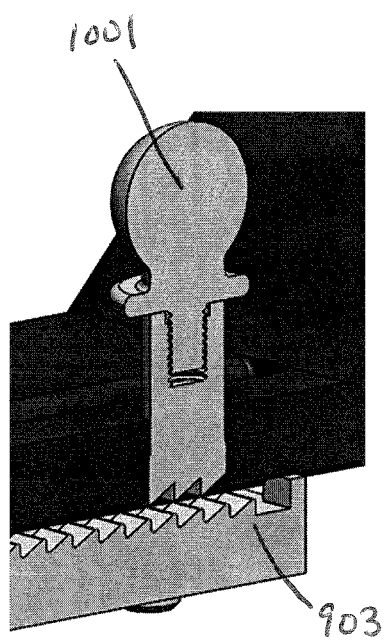

FIGS. 10A-C illustrate conceptually various cross-sectional views of a ratchet mechanism in multiple positions relative to the movable base of FIG. 8 in accordance with the present disclosure;

FIG. 11 illustrates conceptually a ratchet mechanism in released position allowing base to be moved away from the patient in accordance with the present disclosure; and FIGS. 12A-B illustrate conceptually a ratchet mechanism in locked position which prevents the movable base from moving in either direction, using sliding cover in accordance with the present disclosure.

DETAILED DESCRIPTION

Embodiments of the systems and methods are now described in detail with reference to the drawings in which like reference numerals designate identical or corresponding elements in each of the several views. As used herein, the term "user" refers to a doctor, a nurse, or any other care provider and may include support personnel. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so.

Figure 1:
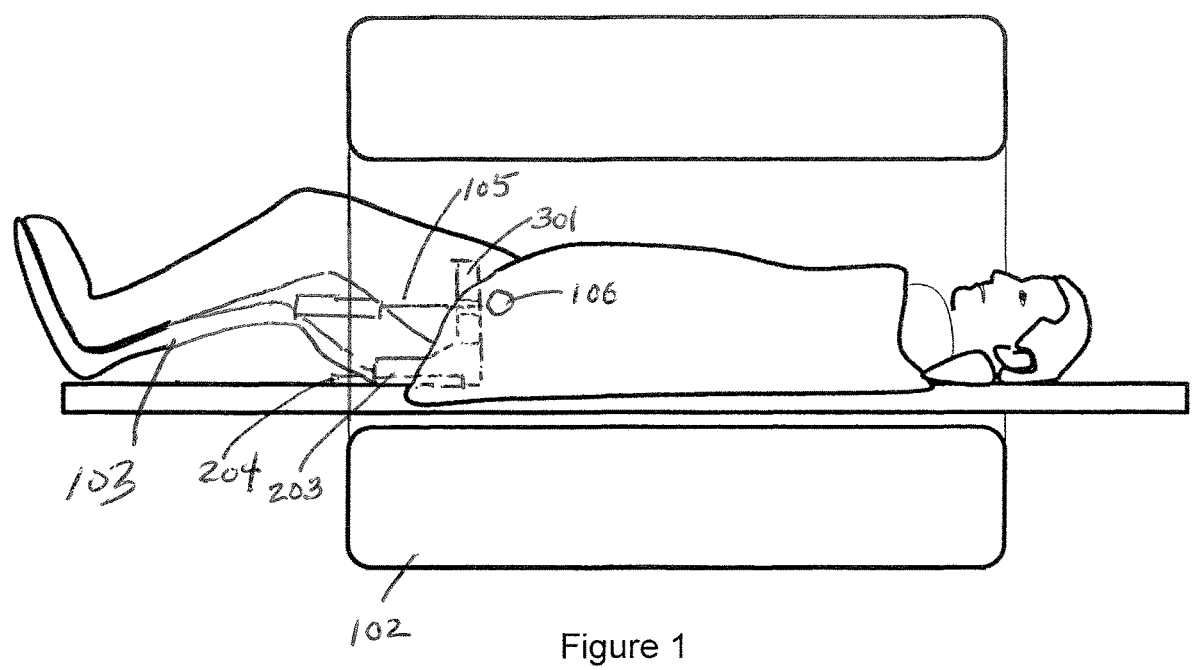
FIG. 1 illustrates conceptually a guide for prostate biopsy in the bore of an MRI scanner.

FIG. 1 illustrates conceptually the process for an MRI-guided trans-perineal approach using a fixed template to guide the needle to targets. In the disclosed method, the patient 101 is placed in the MRI scanner 102 with his feet fixed in stirrups 103. A needle guide 104 is positioned during the procedure after an initial scan of the patient 101. The needle guide is positioned to permit the needle 105 to be inserted into a chosen location within the prostate 106. By accurately targeting MRI-visible regions suspected of containing cancer, the needle guide system and technique disclosed herein will improve the ability to find life-threatening tumors and reduce the chance of unnecessarily treating low-risk cases compared to current methods.

Figure 2:
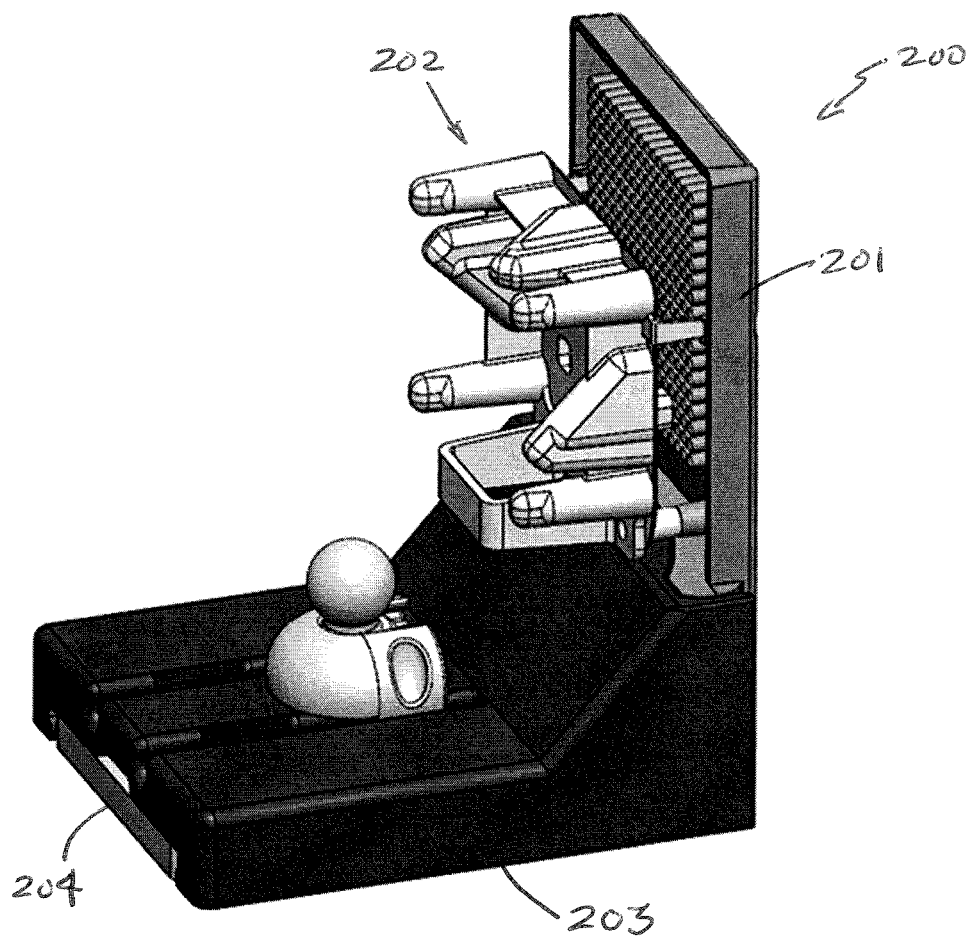
FIG. 2 illustrates conceptually a side, perspective view of a needle guide system in accordance with the present disclosure.

FIG. 2 illustrate conceptually a side, perspective view of a needle guide system 200 in accordance with embodiments of the disclosure. The needle guide system 200 comprises a needle guide component 201, a calibrator component 202 and a movable base component 203 slidable on a rail sub component 204 thereof. The calibrator component 202 is securable to the rear surface (surface facing away from the patient) of the needle guide component 201 and may be removed following an initial scan of the needle guide system. The needle guide component 201 is securable to the movable base component 203 of the system with a plurality of arms 402, as described herein. The movable base component 203 itself is slidable and lockable to the rail sub component 204 on which the base body sits, as explained hereafter in greater detail.

Figure 3:
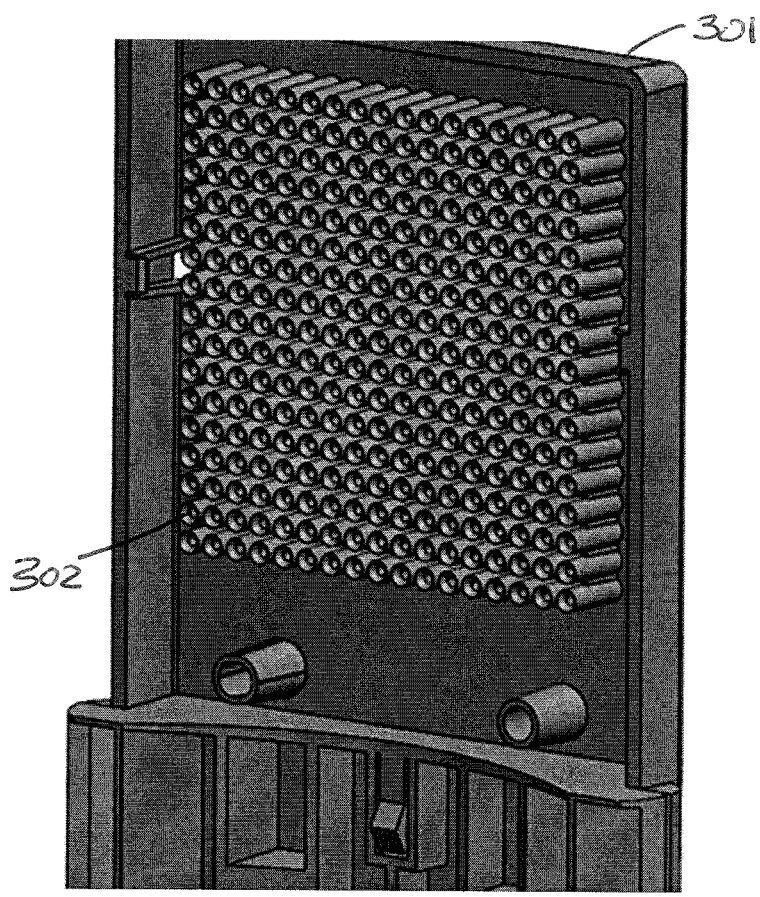
FIG. 3 illustrates conceptually a needle guide component of the needle guide system of FIG. 2 in accordance with the present disclosure.

FIG. 3 illustrates conceptually the needle guide component 201 of the needle guide system of FIG. 2. The needle guide component 201 comprises a needle guide plate 301 with a multiplicity of needle guide channels 302 embedded therein and extending from a first surface thereof through to a second surface thereof. In embodiments, the needle guide component 201 may have a unitary construction manufactured by, for example, injection molding or other processes.

Although the illustrated embodiment comprises a 17×17 matrix of guide channels 302, it will be obvious to those reasonably skilled in the arts that other size matrices may be chosen as well as other pattern arrangements of needle guides, e.g. offset relative to adjacent columns or rows thereof. The diameter of each individual needle guide extending through the needle guide plate may be chosen in accordance with the diameter of the needle to be used with the medical procedure to allow for a smooth passage there through but also adequate support thereof during placement and throughout the procedure. In embodiments, the needle channels have a tapered entrance at the entry surface, e.g., the surface facing away from the patient, and a reduced diameter not substantially larger than the diameter of the needle itself to prevent deflection of the needle upon entry of the perineum surface.

In an illustrative example of a prostate biopsy, a biopsy needle 103 is inserted through one of the guide channels 302 of the needle guide plate 301 from the rear surface to the front surface and into the perineum of the patient. The guide channels 302 may be color coded to match regions highlighted on a computer screen image. The guide channels 302 are joined to the plate 301 of the needle guide body at positions that correspond to the axis of the needle, when the guide is mounted in the scanner. In an illustrative embodiment, both the needle guide plate 301 and guide channels 302 may be made from a substantially rigid material which may be placed in and scanned by an MRI device.

Figure 4:
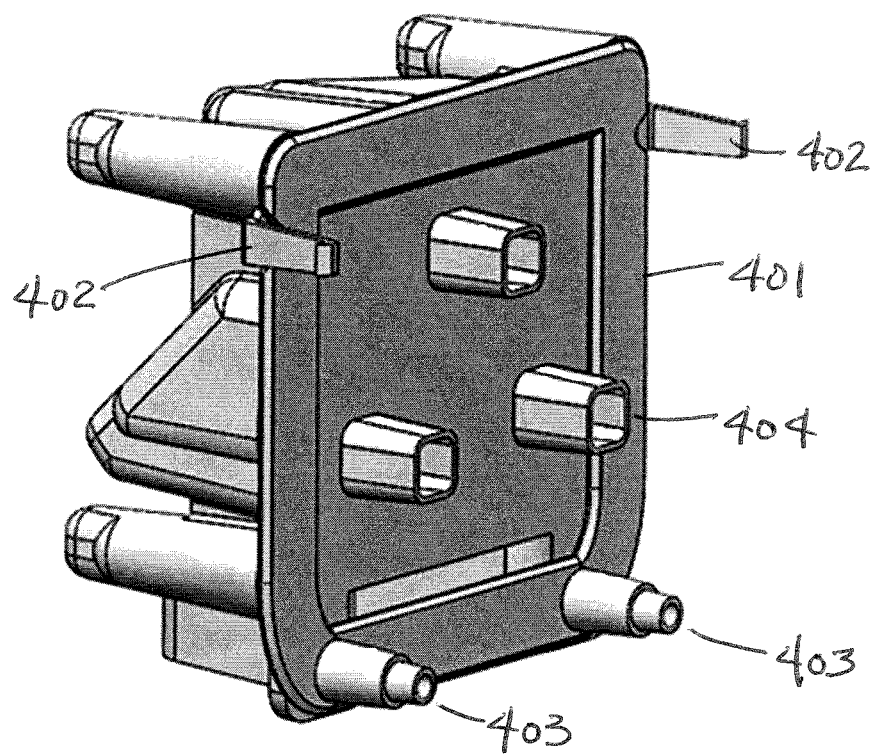
FIG. 4 illustrates conceptually a calibrator component of a needle guide system of FIG. 2 in accordance with the present disclosure.
Figure 5:
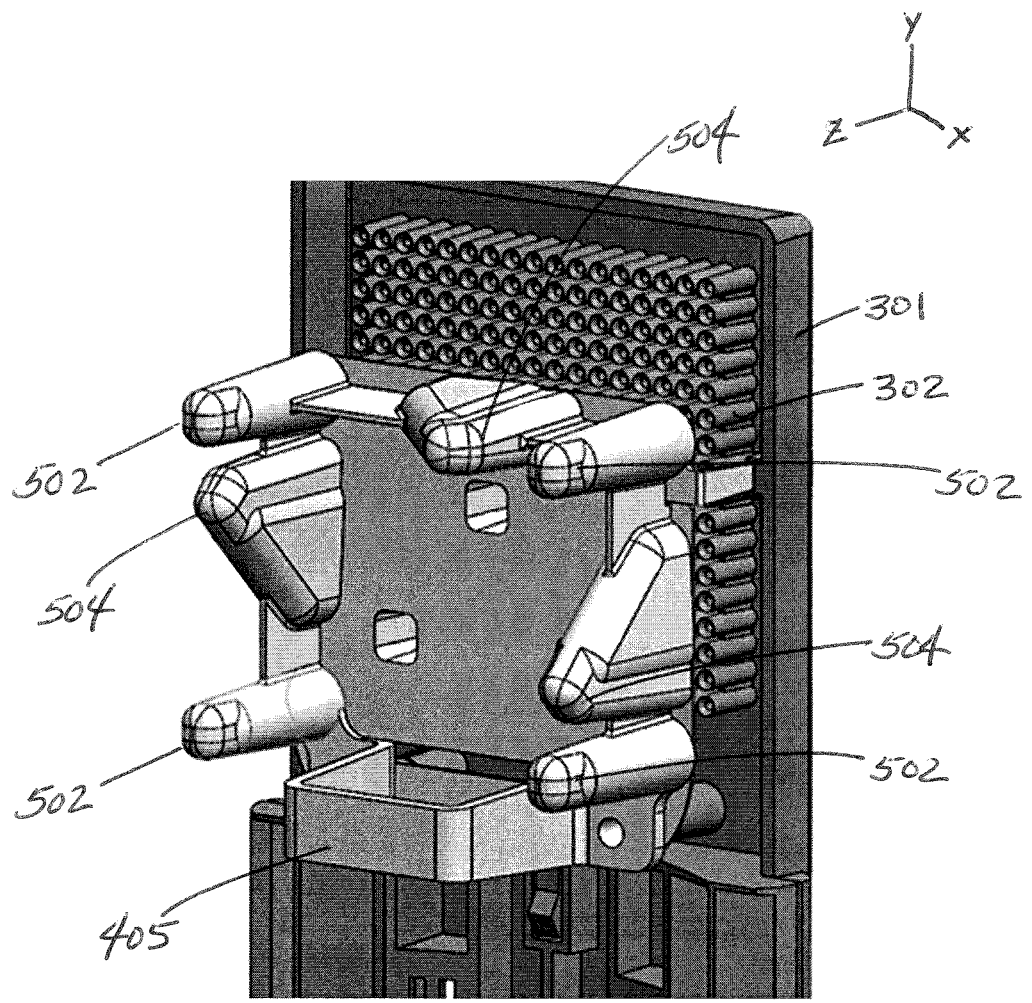
FIG. 5 illustrates conceptually the calibrator component of FIG. 4 engaged with the needle guide component of FIG. 3 in accordance with the present disclosure.

FIG. 4 illustrates conceptually the calibrator component 202 of the needle guide system of FIG. 2. In the illustrated embodiment, the calibrator 202 comprises a generally planar rectangular body 401 having a plurality of arms 402 extending outward from edges thereof, the two arms 402 attachable by frictional engagement with the needle guide plate 301 at different attachment points proximate the perimeter of the needle guide plate. In one embodiment, the arms 402 may be implemented with cantilever clips which frictionally engage features on the surface of the needle guide plate 301, as illustrated in FIG. 5. The calibrator component 202 further comprises a plurality of pins 403 extending outward from thereof, the pins 403 attachable by frictional engagement with complementary mating sockets extending outward from the rear surface of the needle guide plate 301 at different attachment points proximate a lower portion of the needle guide to prevent roll of the needle guide component 201. The calibrator component 202 further comprises a plurality of optional extrusions 404 extending outward from the calibrator component 202 proximate a central portion thereof, the extrusions 404 are designed to prevent the calibrator from rocking against the matrix of guide channels 302 in the needle guide plate 301 when the calibrator component 202 is attached thereto. The calibrator component 202 is designed to be scanned once to calibrate the MRI-system, and then disengaged from the needle guide 201 for the rest of the biopsy procedure. To facilitate such removal, the calibrator component 202 further comprises a handle portion 405 extending outward from the calibrator body 401 on a lower portion thereof to facilitate the removal of the calibrator from the needle guide 201. In the illustrated embodiment, the calibrator component 202 has a unitary construction which may be manufactured by, for example, injection molding or other processes. As with the needle guide 201, the calibrator component 202 may be formed from the material which is substantially rigid material which may be placed in and scanned by an MRI device.

FIG. 5 illustrates the calibrator component 202 of FIG. 4 attached to the needle guide component 201 of FIG. 3 with the arms 402 and pins 403 of the calibrator component frictionally engaged to the rear surface of the needle guide 201 (the side of the needle guide facing away from the patient). A first set of four fiducial markers 502 are positioned at the tips of projections extending from calibrator 202, the locations of such fiducial markers being identifiable by an MRI scanner. A second set of three fiducial markers 504 are positioned at the tips of projections extending from calibrator 202, the locations of such fiducial markers being identifiable by an MRI scanner. In embodiments, the first set of fiducial markers 502 are oriented on axes which are parallel to the axis upon which mobile base 203 translates while the second set of fiducial markers 504 are oriented at angles relative to the plane in which the needle guide plate 301 extends, as illustrated in FIG. 5.

Figure 6:
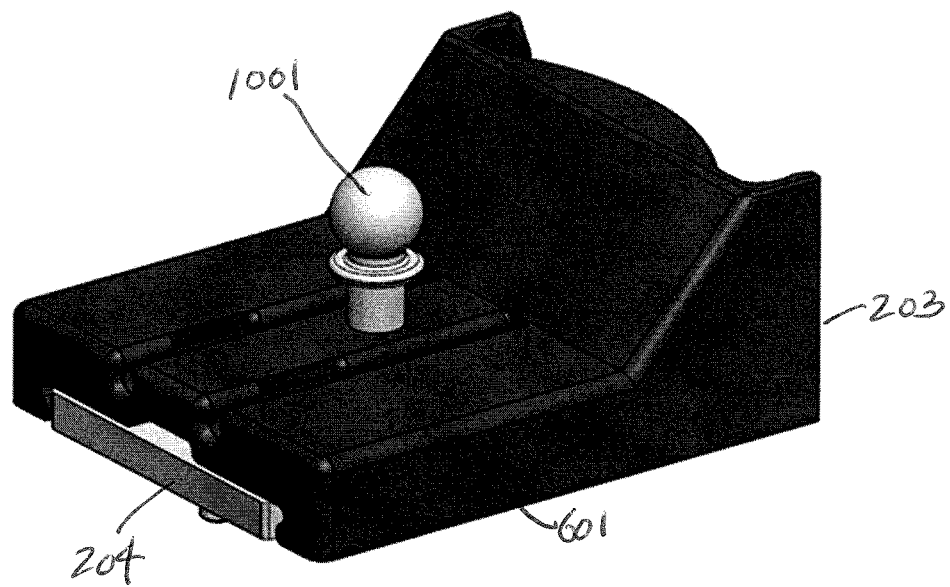
FIG. 6 illustrates conceptually a movable base component of the needle guide system of FIG. 2 in accordance with the present disclosure.
Figure 7:
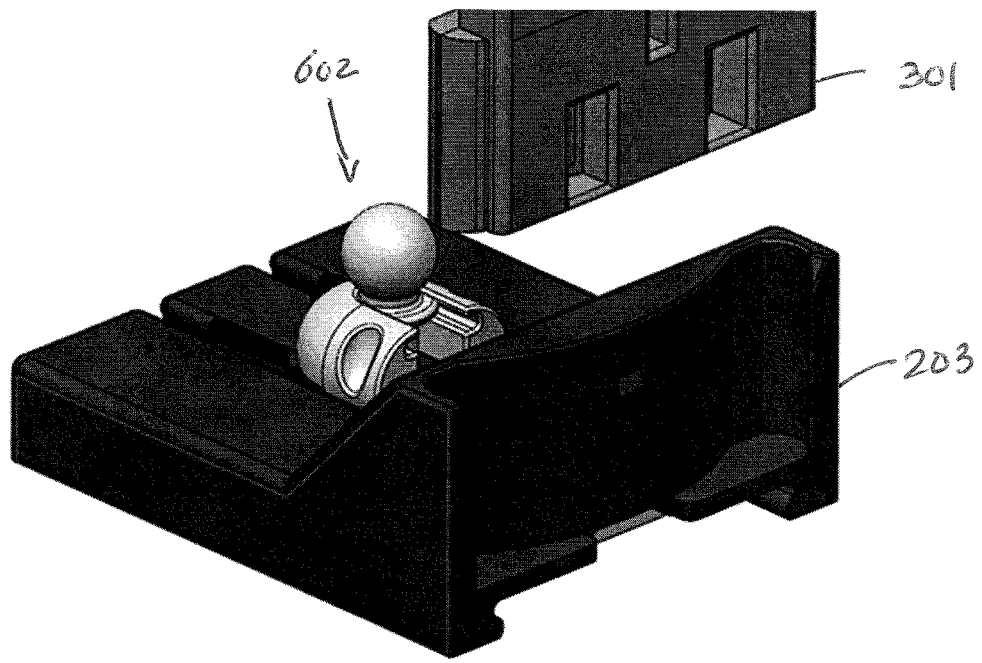
FIG. 7 illustrates conceptually the needle guide component of FIG. 2 relative to the movable base of FIG. 6 in accordance with the present disclosure.

FIGS. 6-7 illustrate conceptually the movable base component 203 of the needle guide system 200 of FIG. 2. In the illustrated embodiment, the movable base component 203 comprises a base body 601, a rail component 204, and a locking mechanism 602 to movably secure the base body to the rail and a locking mechanism housing 701. The base body 601 is slidable over a rail component 204 upon which the base body rests, thereby providing a means for the movable base 203 and needle guide 201 to translate along an axis. The base body 601 further provides support for and is removably attachable to the needle guide 201. One end of the base body includes a cavity 701 having an arcuate side surface into which the bottom end of the needle guide plate 301 is insertable, as illustrated in FIG. 7. In embodiments, the needle guide plate 301 and the base body have complementary surface features to facilitate retaining the needle guide plate 301 in place securely, and to allow a user to clean the entire base with a cloth. As illustrated in FIG. 7, the upgrade portion of these body 601 we are paying fees with these The base body 601 further includes a cavity 702 which may include one or more arcuate surfaces for receiving complementary shaped features at the lower end of needle guide plate 301, beneath the needle guide channel matrix, the two components optionally including complementary engageable features temporarily lock the components relative to each other. The base body 601 further includes a cavity 801 in the underside thereof having at least one side of the cavity shaped to complement features on the exterior surface of the rail component 204, as described below.

Figure 9:
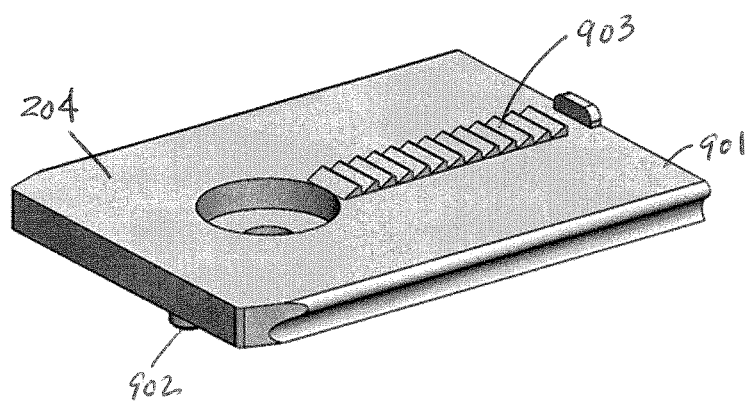
FIG. 9 illustrates conceptually the rail component of the movable base component of FIG. 8 in accordance with the present disclosure.

As illustrated in FIG. 9, the rail component 204 is attached to the patient support and allows the base body 601 to move slidably thereover in one direction. The rail component 204 comprises a substantially flat surface 901 with feet 902 on the under surface thereof, and a toothed ratchet track 903 projecting outward from a top surface thereof and extending along the axial length thereof. One or more edges of rail component 204 have surface features which allow the rail component 204 to be slidably received within cavity in the base body 601 to enable sliding of the base body thereover.

In embodiments, the locking mechanism 602 of the movable base 201 may be implemented with a cylindrical ratchet pin 1001 slidably disposed within a vertical aperture in the base body 601. In the illustrated embodiment, the ratchet pin 1001 has at a top end thereof with a substantially spherical surface to facilitate handling. The ratchet pin 1001 has at the opposite, bottom end thereof with a surface having a plurality of ratchet teeth 1003 angled similar to the ratchet track 903 disposed on the upper surface of the rail component. The locking mechanism 602, when disengaged, allows a user to push the movable base component 203 towards the patient's perineum in one direction, but not to move away from the patient in the opposite direction, allowing for good pressure and positioning against the patient. The locking mechanism 602 can be disengaged if the user wants to translate the movable base component 203 away from the patient by lifting the ratchet pin 1001 of the locking mechanism 602, thereby disengaging the ratchet teeth 1003 from the ratchet track 903. FIGS. 10A-C and 11 illustrate conceptually various cross-sectional views of locking mechanism 602, including the relationship of ratchet pin 101 and ratchet track 903, in multiple positions relative to the movable base component 203, as the ratchet pin 101 is engaged, disengaged and reengaged thereby allowing the base body 601 to move relative to the rail component 204.

FIG. 11 illustrates conceptually a ratchet pin 1001 in a released position allowing movable base 203 to be moved away from the patient. In one embodiment, the locking mechanism 602 further comprises a housing in the form of a essentially U-shaped locking collar 1201 having an arcuate exterior surface with bottom edge features to facilitate slidable positioning of the collar along grooves 604 in the top surface of the base body 601 to facilitate locking of ratchet pin 1001 in place, as necessary. The cover 1201 may have features on the bottom edges thereof that are disposed in a pair of groves 604 in base body 601 which allow the cover 1201 to be removably secured to ratchet pin 1001.

FIGS. 12A-B illustrate conceptually the ratchet pin 1001 in locked position. When positioned about ratchet pin 1001, an interior lip 1202 of locking collar 1201 rests against a flange 1002 on ratchet pin 1001 and prevents the ratchet pin 1001 from becoming disengaged from ratchet track 903, and, therefore, preventing movable base 203 from moving in either direction. Sliding the collar 1201 away from ratchet pin 1001 allows the ratchet pin 1001 to be pulled upward and disengaged from ratchet track 903, thereby allowing the movable base 203 to move relative to rail component 204, which is presumably fixed relative to the patient.

In embodiments, all components of the disclosed needle guide system 200 may be formed from substantially rigid, sterilizable and magnetic resonance compatible materials, such as natural or synthetic resins with antimicrobial properties.

In an alternative embodiment, one or more of the needle guide channel 302 may include a central needle guide channel and multiple side needle guide channels, and, additionally, the needle guide plate 301 may be custom formed, the structure and techniques of such concepts being disclosed in U.S. Patent Publication US-2017-0209170-A1, Ser. No. 15/418,292, entitled Custom Needle Guide Apparatus And Method For Manufacture In A Medical Procedure, and International Application Number PCT/US17/15420, International Publication Number US 2017/132553 A1, the subject matter contents of which are incorporated herein by this reference for all purposes.

The disclosed needle guide system facilitates a method for directing needle entry during a medical procedure, such as an MRI-guided prostate biopsy, while the patient remains in the bore of the MRI scanner. In one embodiment the method comprises securing the rail component of the movable base to a surface having a fixed relationship to the bore of the MRI scanner. Next, the calibration component 202 is used to slide the bottom end XX of the needle guide plate 301 into the upright cavity 702 at the back of the movable base body 203 until plate 301 is frictionally secured to the base body with the calibration component 202 remaining secured to the plate 301. Next, the ratchet pin 1001 is released and the movable base body 203 is positioned along the axis parallel to the plurality of needle guide channels so that needle guide plate 301 is disposed adjacent to patient's perineum to decrease the distance between the needle guide plate and the skin surface to prevent deflection of the needles as the needle enters the body. Once the needle guide plate 301 is secured in place, the needle guide plate with the calibration component attached to the needle guide plate is scanned so that the fiducial marker therein provide a reference frame image for locating the needle guide channels relative to the organ to be biopsied. Such location can be computed from the know fixed location of the fiducial markers in the reference frame relative to the coordinated of the MRI scanner bore and using an offset value for the location of the matrix of guide channels. Once scanned at least for the first set of needles, the calibration component can be disengaged from the needle guide plate 301. Finally, a needle is inserted into one of the plurality of needle guide channels. In embodiments, target locations for needle insertion can be identified in a reference frame of the scanner using initial images and pre-operative multi-parameter MRI, and needle trajectories through the needle guide plate selected accordingly, e.g. computed from the know fixed location of the fiducial markers in the reference frame relative to the coordinates of the MRI scanner bore and using an offset value for the location of the matrix of needle guide channels.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. It will be obvious to those reasonably skilled in the art that modifications to the apparatus and process disclosed here in may occur, including substitution of various component values, without parting from the true spirit and scope of the disclosure, for example, the disclosed apparatus and techniques can be extended for non-image guided procedures, procedures other than biopsies of the prostate, and with image guided procedures using imaging technologies other than MRI imaging. Those skilled in the art will envision other modifications within the scope and spirit of the claims appended hereto.

What is claimed is:

1. A sterile needle guide system for use during medical procedure comprising:
   a needle guide plate extending in a plane and having a plurality tubular needle guides extending through the plate at an angle to the plane of the plate; and
   a movable base translatable along an axis normal to the plane of the plate and defining features to removably receiving the plate, the movable base comprising:
   a base body;
   a rail component over which the base body is movably coupled; and
   a ratchet mechanism for releasably securing the base body to the rail component.

2. The system of claim 1 further comprising:
   a calibrator attachment removably securable to the needle guide plate.

3. The system of claim 1 wherein the plurality tubular needle guides extend through the plate at an angle normal to the plane of the plate.

4. The system of claim 1 wherein the ratchet mechanism comprises:
   a locking pin disposed within an aperture in the base body, the locking pin having a plurality of teeth at a first end thereof; and
   a track of teeth extending on a surface of the rail component, the track of teeth having complementary mating features with the teeth at the first end of the locking pin.

5. The system of claim 4 wherein the ratchet mechanism further comprises:
   a locking pin collar at least partially securable about the locking pin for maintaining the locking pin within the aperture in the base body.

6. A sterile needle guide kit for use during medical procedure comprising:
   a needle guide plate extending in a plane and having a plurality tubular needle guides extending through the plate at an normal angle to the plane of the plate;
   a movable base translatable along an axis relative to the plane of the plate and defining features to removably receiving the plate, the movable base comprising:
   a base body;
   a rail component over which the base body is movably coupled; and
   a ratchet mechanism for releasably securing the base body to the rail componen; and
   a calibrator attachment removably securable to the needle guide plate.

7. The kit of claim 6 wherein the ratchet mechanism comprises:
   a locking pin disposed within an aperture in the base body, the locking pin having a plurality of teeth at a first end thereof; and
   a track of teeth extending on a surface of the rail component, the track of teeth having complementary mating features with the teeth at the first end of the locking pin.

8. The kit of claim 7 wherein the ratchet mechanism further comprises:
   a locking pin collar at least partially securable about the locking pin for maintaining the locking pin within the aperture in the base body.

9. A method for directing needle entry during a medical procedure comprising:
   A) providing a movable base comprising a base body, a rail component over which the base body is movably coupled, and a ratchet mechanism for releasably securing the base body to a rail component having an axis, the movable base removably securable to a needle guide plate having a plurality of fiducial markers in a plane normal to the axis and a plurality of needle guide channels extending through the needle guide plate parallel to the axis;
   B) securing the movable base along the axis by securing the rail component to the movable base;
   C) securing the sterile needle guide plate to the movable base;
   D) positioning the movable base along the axis;
   E) obtaining a frame of reference from the plurality of fiducial markers attached to the needle plate;
   F) determining a position of at least one needle guide channel relative to the fiducial markers; and
   G) inserting a needle into at least one needle guide channels.

10. The method of claim 9 wherein D) comprises:
    D1) translating the movable base along the axis, and
    D2) securing the movable base to the rail component with the ratchet mechanism.

11. The method of claim 10 wherein F) comprises

F1) capturing a reference image of the fiducial markers; and

F2) determining a position of at least one needle guide channel from the know fixed location of the fiducial markers in the reference image relative to the coordinated of the MRI scanner bore and using an offset value for the location of the matrix of guide channels.

12. The system of claim 2 wherein the calibrator attachment comprises:

a calibrator body having a handle extending outward there.

13. The system of claim 2 wherein the calibrator attachment comprises:

a calibrator body having a plurality of arms extending outward from the calibrator body for frictionally engaging the needle guide plate.

14. The system of claim 2 wherein the calibrator attachment comprises:

a calibrator body having a plurality of pins extending outward from the calibrator body for frictionally engaging the needle guide plate.

15. The system of claim 5 wherein the base body of the movable base comprises at least one groove in a surface thereof for slidably receiving at least a portion of the locking pin collar.

\* \* \* \* \*